United States Patent
Horita et al.

(10) Patent No.: US 11,963,732 B2
(45) Date of Patent: Apr. 23, 2024

(54) DOCTOR-SIDE CONTROL APPARATUS AND SURGICAL SYSTEM

(71) Applicant: MEDICAROID CORPORATION, Kobe (JP)

(72) Inventors: Shiro Horita, Kobe (JP); Takahiro Ueda, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 422 days.

(21) Appl. No.: 17/228,607

(22) Filed: Apr. 12, 2021

(65) Prior Publication Data

US 2021/0315651 A1 Oct. 14, 2021

(30) Foreign Application Priority Data

Apr. 13, 2020 (JP) ................................. 2020-071565

(51) Int. Cl.
*A61B 1/00* (2006.01)
*A61B 34/37* (2016.01)
*B25J 3/00* (2006.01)

(52) U.S. Cl.
CPC ................. *A61B 34/37* (2016.02); *B25J 3/00* (2013.01)

(58) Field of Classification Search
CPC ......... A61B 34/37; A61B 34/35; A61B 34/30; A61B 2034/305; B25J 3/00; B25J 5/007; B25J 13/04; B25J 13/06
USPC ......................................................... 600/101
See application file for complete search history.

(56) References Cited

U.S. PATENT DOCUMENTS

| | | | |
|---|---|---|---|
| 7,533,892 B2 | 5/2009 | Schena et al. | |
| 7,909,122 B2 | 3/2011 | Schena et al. | |
| 8,418,073 B2 | 4/2013 | Mohr et al. | |
| 8,448,729 B2 | 5/2013 | Schena et al. | |
| 9,415,510 B2 | 8/2016 | Hourtash et al. | |
| 9,615,883 B2 | 4/2017 | Schena et al. | |
| 9,680,333 B1* | 6/2017 | Brooks | H02J 7/00714 |
| 9,907,619 B2 | 3/2018 | Hourtash et al. | |
| 10,092,344 B2 | 10/2018 | Mohr et al. | |
| 10,231,792 B2 | 3/2019 | Shiels et al. | |
| 10,251,715 B2 | 4/2019 | Hourtash et al. | |
| 10,603,119 B2 | 3/2020 | Ross et al. | |
| 10,687,908 B2 | 6/2020 | Hourtash et al. | |
| 2017/0087730 A1 | 3/2017 | Robinson et al. | |

(Continued)

FOREIGN PATENT DOCUMENTS

JP 2008-86542 A 4/2008
JP 2016-516487 A 6/2016

(Continued)

*Primary Examiner* — Timothy J Neal
*Assistant Examiner* — James Edward Boice
(74) *Attorney, Agent, or Firm* — METROLEX IP LAW GROUP, PLLC

(57) ABSTRACT

A remote control apparatus (a doctor-side control apparatus) according to an embodiment is provided at a position away from a medical manipulator including an arm to which a medical instrument is attached and is configured to remotely operate the medical manipulator. Each of a plurality of wheels that are provided at a bottom surface of the control apparatus is configured to move a control apparatus main body in a first direction parallel to a floor surface on which the control apparatus main body is placed and in a second direction parallel to the floor surface and orthogonal to the first direction.

18 Claims, 5 Drawing Sheets

(56) References Cited

U.S. PATENT DOCUMENTS

| | | |
|---|---|---|
| 2017/0100197 A1* | 4/2017 | Zubiate .................. A61B 34/37 |
| 2018/0125439 A1 | 5/2018 | Nabeta et al. |
| 2018/0353247 A1 | 12/2018 | Ishihara et al. |
| 2019/0038335 A1 | 2/2019 | Mohr et al. |
| 2019/0160865 A1 | 5/2019 | Bhat et al. |
| 2020/0129250 A1* | 4/2020 | Kapadia .................. A61B 34/25 |
| 2020/0179067 A1 | 6/2020 | Ross et al. |
| 2020/0289213 A1 | 9/2020 | Swarup et al. |
| 2021/0022821 A1* | 1/2021 | Chamorro .............. A61B 50/10 |
| 2021/0187749 A1* | 6/2021 | Lee ........................ B25J 9/0009 |
| 2021/0205040 A1* | 7/2021 | Hassan ................... B25J 13/04 |

FOREIGN PATENT DOCUMENTS

| | | |
|---|---|---|
| JP | 2017-23185 A | 2/2017 |
| JP | 2017-512529 A | 5/2017 |
| JP | 2020-6231 A | 1/2020 |

* cited by examiner

DOCTOR-SIDE CONTROL APPARATUS AND SURGICAL SYSTEM

CROSS REFERENCE TO RELATED APPLICATIONS

This application claims priority based on 35 USC 119 from prior Japanese Patent Application No. 2020-071565 filed on Apr. 13, 2020, the entire contents of which are incorporated herein by reference.

BACKGROUND

The disclosure relates to a doctor-side control apparatus and a surgical system.

In a related art, a robotic surgical system that includes a surgical robot and a surgeon-side console configured to remotely control the surgical robot is disclosed. (See Patent Document 1: Japanese translation of PCT international Application No. 2016-516487)

In the robotic surgical system disclosed in Patent Document 1, tools (medical instruments) are attached to arms of the surgical robot. The surgeon-side console is located at a position away from the surgical robot. The surgeon-side console is provided with a display and an input device. By operating the input device of the surgeon-side console by the surgeon, the tools attached to the arms of the surgical robot are operated.

Even though Patent Document 1 does not explicitly describe, it is known that the surgeon-side console (surgeon console) of the Da Vinci Xi Surgical System, which is a robotic surgery system manufactured by the applicant of Patent Document 1, can only be moved in the left-right direction on the floor surface on which the surgeon-side console is arranged (one direction orthogonal to a direction in which the surgeon faces the surgeon-side console).

[Patent Document 1] Japanese translation of PCT international Application No. 2016-516487

SUMMARY

In a case where the surgeon-side console can be moved only in the left-right direction on the floor surface as in the robotic surgery system of Patent Document 1, it may take time to locate the surgeon-side console in a desired position. Therefore, it may be desired to improve the convenience of moving the surgeon-side console (doctor-side control apparatus).

An object of the disclosure is to provide a doctor-side control apparatus and a surgical system that can improve the convenience of mobility.

A first aspect of the disclosure is a doctor-side control apparatus to be provided at a position away from a patient-side apparatus that includes an arm to which a medical instrument is attached and to remotely control the patient-side apparatus. The doctor-side control apparatus includes: a control apparatus main body; and a plurality of wheels provided at a bottom surface of the control apparatus main body. Each of the plurality of wheels is configured to move the control apparatus main body in a first direction parallel to a floor surface on which the control apparatus main body is placed and in a second direction parallel to the floor surface and orthogonal to the first direction.

According to the first aspect, as described above, at the bottom surface of the control apparatus main body, the plurality of wheels are provided each of which is configured to move the control apparatus main body in the first direction parallel to the floor surface on which the control apparatus main body is placed and in the second direction parallel to the floor surface and orthogonal to the first direction. With this configuration, the control apparatus main body can be moved in plural directions, that is, the first direction and the second direction orthogonal to each other along the floor surface. Accordingly, the doctor-side control apparatus (the control apparatus main body) can be easily disposed at a desired position even in a relatively narrow operating room. As a result, it is possible to improve the convenience of moving the doctor-side control apparatus.

A second aspect of the disclosure is a surgical system that includes: a patient-side apparatus that includes an arm to which a medical instrument is attached; and a doctor-side control apparatus provided at a position away from the patient-side apparatus and configured to remotely control the patient-side apparatus. The doctor-side control apparatus includes: a control apparatus main body; and a plurality of wheels provided at a bottom surface of the control apparatus main body. Each of the plurality of wheels is configured to move the control apparatus main body in a first direction parallel to a floor surface on which the control apparatus main body is placed and in a second direction parallel to the floor surface and orthogonal to the first direction.

According to the second aspect, as described above, at the bottom surface of the control apparatus main body, the plurality of wheels are provided which are configured to move the control apparatus main body in the first direction parallel to the floor surface on which the control apparatus main body is placed and in the second direction parallel to the floor surface and orthogonal to the first direction. With this configuration, the control apparatus main body can be moved in plural directions, that is, the first direction and the second direction orthogonal to each other along the floor surface. Accordingly, the doctor-side control apparatus (the control apparatus main body) can be easily disposed at a desired position even in a relatively narrow operating room. As a result, it is possible to provide the surgical system that can improve the convenience of moving the doctor-side control apparatus.

According to at least one of the aspects described above, it is possible to improve the convenience of moving the doctor-side control apparatus.

DETAILED DESCRIPTION

Figure 1:
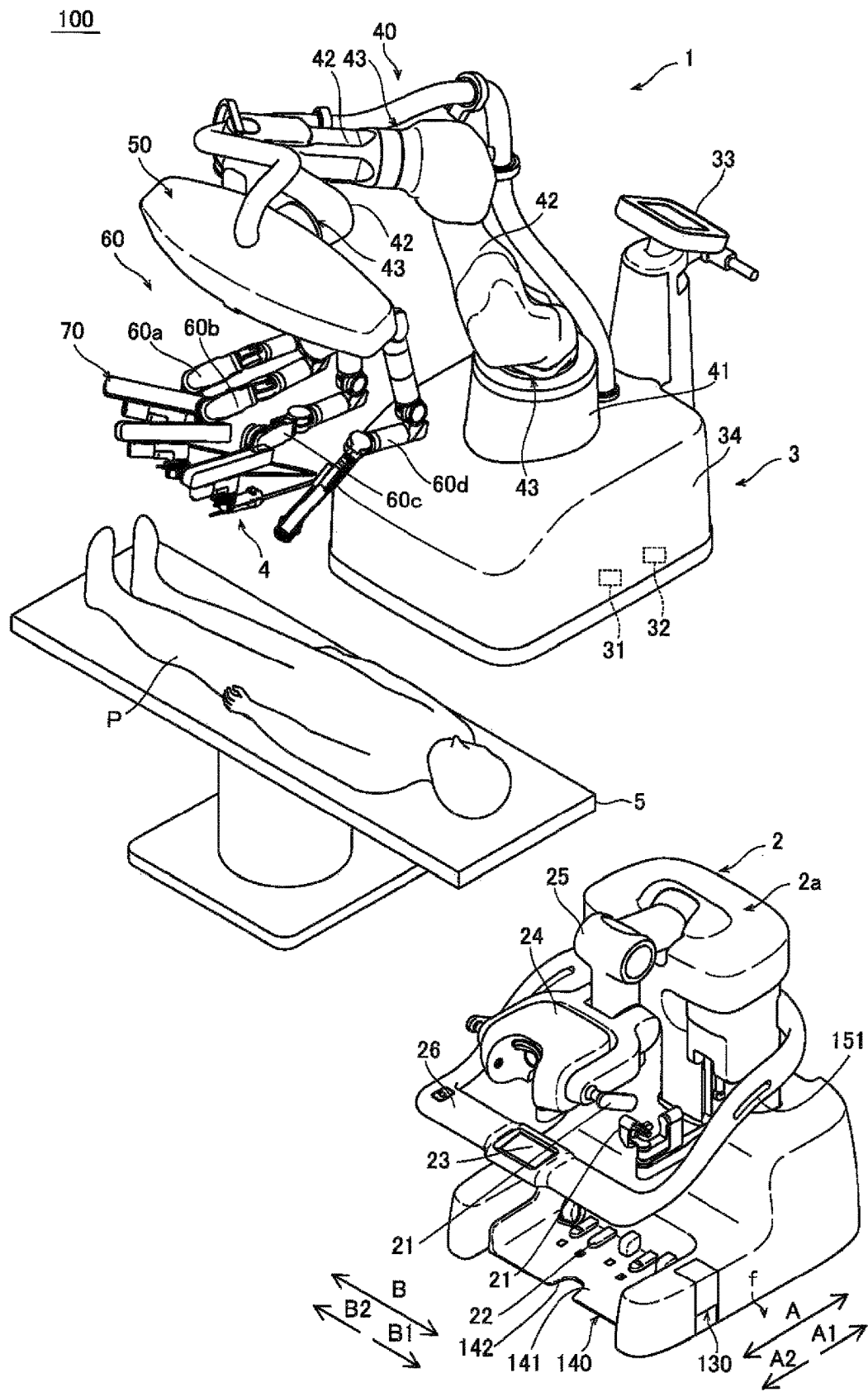
FIG. 1 is a diagram illustrating a view of a configuration of a surgical operation system according to an embodiment.

Descriptions are provided hereinbelow for embodiments based on the drawings. In the respective drawings referenced herein, the same constituents are designated by the same reference numerals and duplicate explanation concerning the same constituents is omitted. All of the drawings are provided to illustrate the respective examples only.

A configuration of a surgical operation system 100 according to an embodiment is described with reference to FIGS. 1 to 9. The surgical operation system 100 includes a medical manipulator 1 serving as a patient-side system and a remote control apparatus 2 serving as an operator-side apparatus to operate the medical manipulator 1. The medical manipulator 1 is provided with a medical trolley 3 and is thus configured to be movable. The remote control apparatus 2 is located at a position away from the medical manipulator 1. The medical manipulator 1 is configured to be remotely operated by the remote control apparatus 2. An operator (a doctor) inputs to the remote control apparatus 2 an instruction that causes the medical manipulator 1 to perform a desired operation. The remote control apparatus 2 transmits the input instruction to the medical manipulator 1. The medical manipulator 1 operates in response to the received instruction. The medical manipulator 1 is arranged in a surgery room, as a sterile field, which is sterilized. Note that the medical manipulator 1 is an example of a "patent-side apparatus." The remote control apparatus 2 is an example of a "doctor-side control apparatus." The surgical operation system 100 is an example of a "surgical system."

The remote control apparatus 2 is located at a position away from the medical manipulator 1 including arms 60 to which medical instruments 4 are attached. The remote control apparatus 2 is configured to remotely control the medical manipulator 1. The remote control apparatus 2 is placed inside the surgery room or outside the surgery room, for example. The remote control apparatus 2 includes a control apparatus main body 2a, operation manipulator arms 21, operation pedals 22, a touch panel 23, a monitor 24, a support arm 25, and a support bar 26. The operation manipulator arms 21 constitute operation handles for the operator to input the instruction. The monitor 24 is a display device of a scope type configured to display an image captured by an endoscope. The support arm 25 supports the monitor 24 in such a manner that the height of the monitor 24 is adjusted to the height of the face of the operator. The touch panel 23 is provided on the support bar 26. When a sensor(s) provided in the vicinity of the monitor 24 detects the head of the operator, the medical manipulator 1 is allowed to be operated by the remote control apparatus 2. The operator operates the operation manipulator arms 21 and the operation pedals 22, while viewing the surgical site displayed on the monitor 24. With this, the instruction is input to the remote control apparatus 2. The instruction that is input to the remote control apparatus 2 is transmitted to the medical manipulator 1

Figure 2:
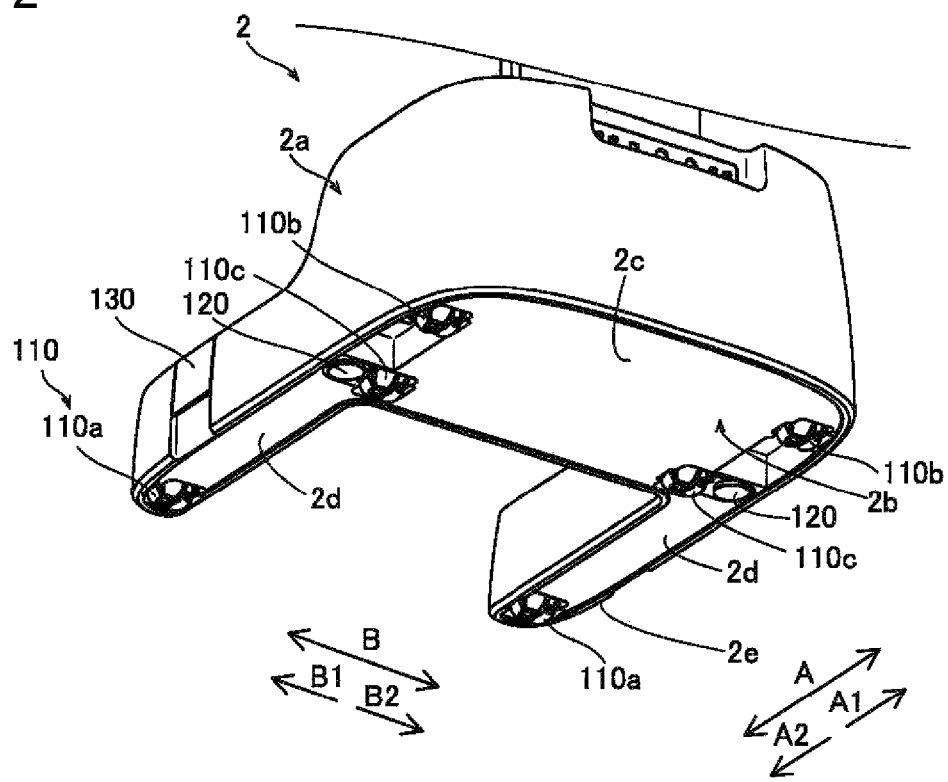
FIG. 2 is a diagram illustrating a perspective view of a remote control apparatus according to an embodiment as seen from below.
Figure 3:
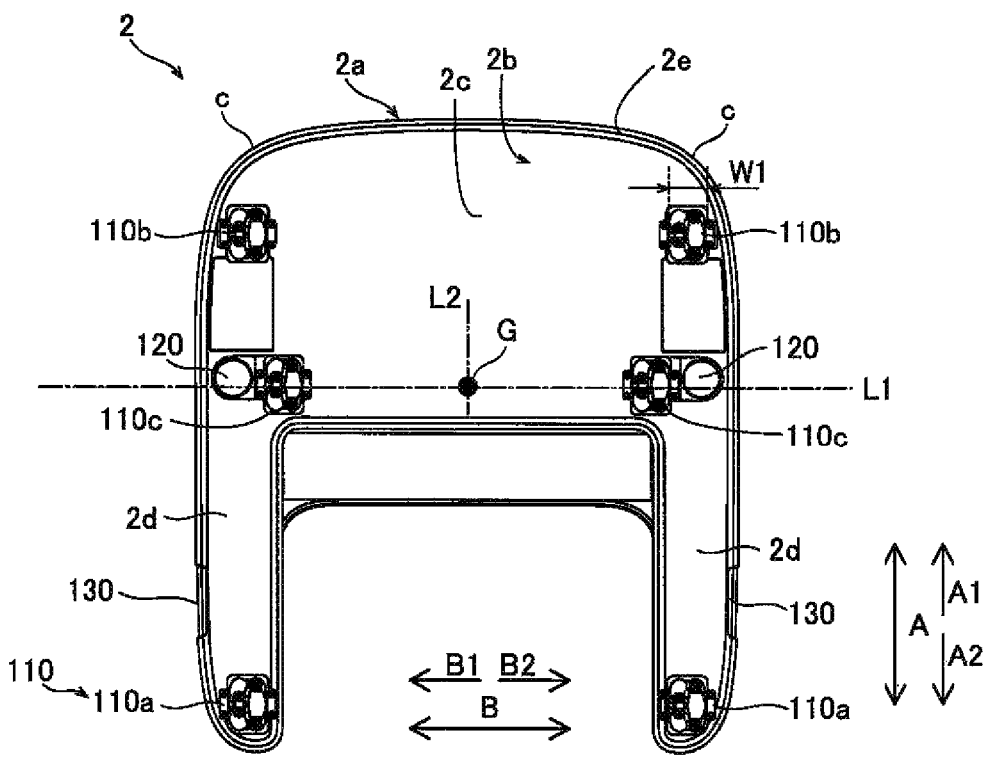
FIG. 3 is a diagram illustrating a bottom view of the remote control apparatus according to an embodiment.

In the embodiment, as illustrated in FIGS. 2 and 3, the remote control apparatus 2 is provided with a plurality (six in the embodiment) of wheels 110. The plurality of wheels 110 are provided at the lower surface 2b of the control apparatus main body 2a and configured to allow the control apparatus main body 2a to move in an A direction along the floor surface f on which the control apparatus main body 2a is placed and in a B direction orthogonal to the A direction along the floor surface f. Here, the A direction is a direction in which the control apparatus main body 2a and the doctor who controls the control apparatus main body 2a are opposed to (face) each other. Note that the A direction and the B direction are examples of a "first direction" and a "second direction", respectively.

Figure 4:
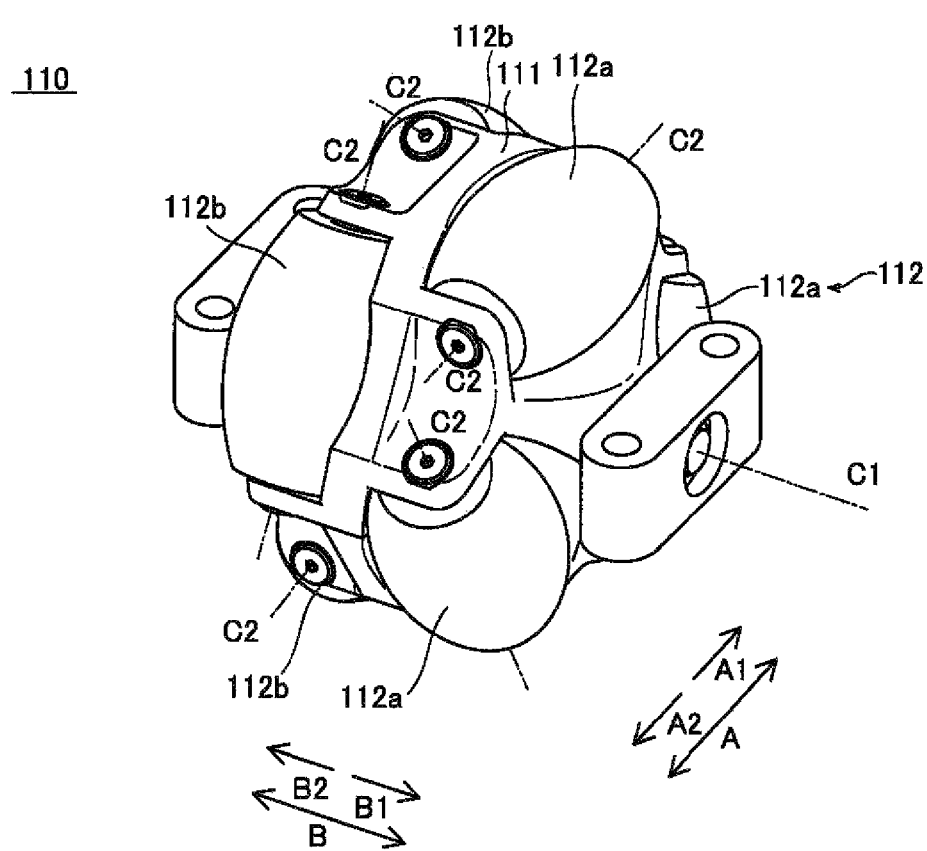
FIG. 4 is a diagram illustrating a perspective view of a wheel of the remote control apparatus according to an embodiment.
Figure 5:
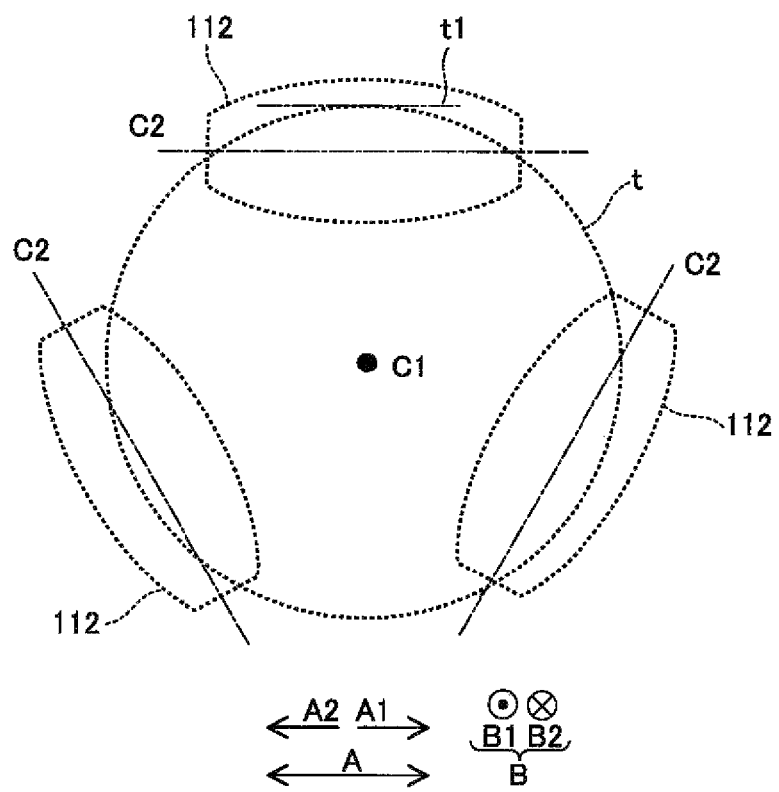
FIG. 5 is a diagram illustrating a view a relationship between a rotation trajectory of the wheel of the remote control apparatus and rotation axes of roller parts.

In the embodiment, as illustrated in FIG. 4, the wheel 110 includes a wheel body 111 that rotates about an axis C1 thereof parallel to the B direction and a plurality of roller parts 112 that are arranged at substantially equal angular intervals along an outer circumferential portion of the wheel body 111 and rotate about axes C2 thereof parallel to the tangent line t1 (see FIG. 5) of the circumferential locus t (see FIG. 5) on which the wheel body 111 rotates. The plurality of roller parts 112 are attached to the wheel body 111. When the control apparatus main body 2a is moved in the A direction, the wheel body 111 rotates about the axis C1 thereof parallel to the B direction, and the plurality of roller parts 112 are revolved along with the rotation of the wheel body 111. That is, the plurality of roller parts 112 do not rotate (spin) about the axes C2 thereof but travel about the axis C1 along with the rotation of the wheel body 111. To the contrary, when the control apparatus main body 2a is moved in the B direction, the wheel body 111 does not rotate, and the plurality of roller parts 112 rotate about the axes C2 thereof parallel to the tangent line t1 of the circumferential locus t of the wheel body 111. That is, the wheel 110 is composed of an omni wheel (registered trademark).

In the embodiment, the plurality of roller parts 112 includes one-side roller parts 112a and the other-side roller parts 112b. The one-side roller parts 112a are provided on one side in the B direction (B1 side) on the outer circumferential portion of the wheel body 111 and arranged along the outer circumferential portion of the wheel body 111 at substantially equal angular intervals. The other-side roller parts 112b are arranged on the other side in the B direction (B2 side) on the outer circumferential portion of the wheel body 111 and arranged along the outer circumferential portion of the wheel body 111 at substantially equal angular intervals in such a manner that the other-side roller parts 112b are provided at positions different from the one-sided roller parts 112a in the circumferential direction of the wheel body 111. Specifically, the plurality of one-side roller parts 112a are three and are arranged at intervals of approximately 120 degrees. Also, the plurality of the other-side roller parts 112b are three and are arranged at intervals of approximately 120 degrees. When viewed from the B direction, the one-side roller parts 112a and the other-side roller parts 112b are alternatingly arranged along the circumferential direction of the wheel body 111.

In the embodiment, as illustrated in FIG. 3, the bottom surface 2b of the control apparatus main body 2a is formed in a substantially U-shape including a body portion 2c and a pair of leg portions 2d extend from the body portion 2c along the floor surface f. The plurality of wheels 110 are provided at the pair of leg portions 2d and the body portion 2c. Each of the pair of leg portions 2d is provided along the A direction. The body portion 2c has a substantially rectangular shape with the long side thereof in the B direction. Each of corner portions of the body portion 2c on the A1 side has a rounded shape.

In the embodiment, the plurality of wheels 110 include a pair of first wheels 110a, a pair of second wheels 110b, and a pair of third wheels 110*c*. The pair of first wheels 110*a* are respectively provided at end portions (A2-side end portions) of the pair of leg portions 2*d*. The pair of second wheels 110*b* are respectively provided in the body portion 2*c* on opposite sides (A1-side) from the pair of leg portions 2*d*. The pair of third wheels 110*c* are respectively provided in the body portion 2*c* on the sides (A2-side) closer to the pair of leg portions 2*d*. The pair of second wheels 110*b* are arranged at positions shifted to the A2 side from the A1-side corner portions c of the body portion 2*c*. This makes it possible to prevent the second wheels 110*b* from coming into contact with an outer cover portion 2*e* of the control apparatus main body 2*a*. The pair of the first wheels 110*a* (the pair of the second wheels 110*b*, and the pair of the third wheels 110*c*) are arranged at positions symmetrical with respect to the line L2 passing through the gravity center G along the A direction.

In the embodiment, as viewed from the bottom surface 2*b* of the control apparatus main body 2*a*, at least one of the plurality of wheels 110 is arranged on a straight line L1 which is parallel to the B direction and passes through the center of gravity G of the control apparatus main body 2*a*. Specifically, as viewed from the bottom surface 2*b* of the control apparatus main body 2*a*, the pair of third wheels 110*c* are arranged on the straight line which is parallel to the B direction and passes through the gravity center G of the control apparatus main body 2*a*.

In the embodiment, in the bottom surface 2*b* of the control apparatus main body 2*a*, the third wheels 110*c* are arranged on inner side than the first wheels 110*a* and the second wheels 110*b*. Specifically, the third wheels 110*c* are arranged on the inner side than the first wheels 110*a* and the second wheels 110*b* in the B direction by the length approximately same as the width W1 of the first and second wheels 110*a* and 110*b* in the B direction.

Figure 6:
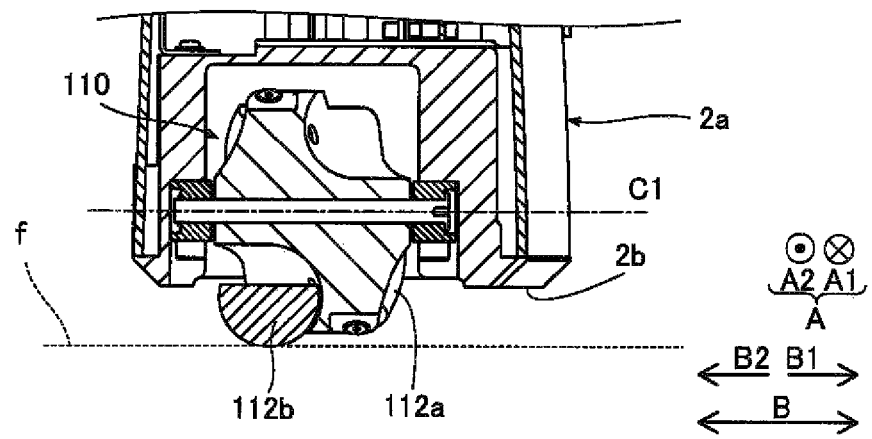
FIG. 6 is a diagram illustrating a cross sectional view of the wheel of the remote control apparatus according to an embodiment.

As illustrated in FIG. 6, a part of each wheel 110 is protruded downwardly from the bottom surface 2*b* of the control apparatus main body 2*a*. With this configuration, the bottom surface 2*b* of the control apparatus main body 2*a* is arranged with being spaced away from the floor surface f.

In the embodiment, as illustrated in FIG. 3, the control apparatus main body 2*a* is provided with a movement restriction part 120 that is movable in a direction perpendicular to the floor surface f to switch between a state that allows movement of the control apparatus main body 2*a* and a state that restricts the movement of the control apparatus main body 2*a*. As viewed from the bottom surface 2*b* of the control apparatus main body 2*a*, the movement restriction part 120 is provided on the straight line L1 that is parallel to the B direction and passes through the gravity center G of the control apparatus main body 2*a*. Specifically, the movement restriction part 120 includes a pair of movement restriction parts 120. The pair of movement restriction parts 120 are arranged at positions symmetrical with reference to the line L2 passing through the gravity center G along the A direction.

Figure 7:
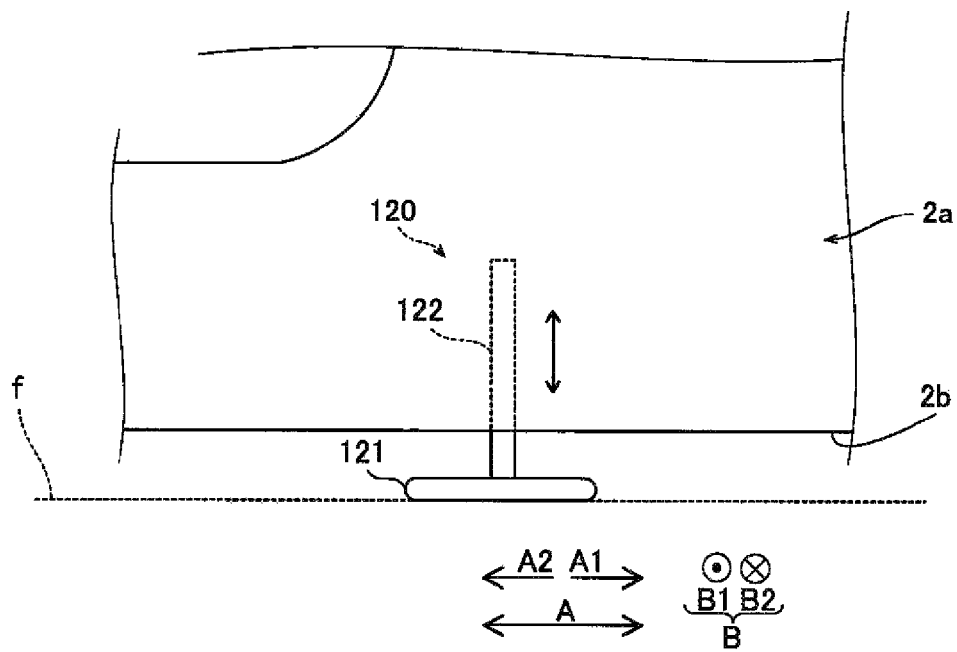
FIG. 7 is a conceptual diagram illustrating a view of a movement restriction part of the remote control apparatus according to an embodiment.

As illustrated in FIG. 7, each of the movement restriction parts 120 is composed of, for example, a disk-shaped rubber member 121 and a shaft member 122 to move the rubber member 121 in the direction perpendicular to the floor surface f. When the movement restriction parts 120 are in contact with the floor surface f, the movement of the control apparatus main body 2*a* is restricted. When the movement restriction parts 120 are spaced away from the floor surface f, the movement of the control apparatus main body 2*a* is allowed.

In the embodiment, as illustrated in FIG. 3, the movement restriction parts 120 are provided on outer sides than the third wheels 110*c* in the bottom surface 2*b* of the control apparatus main body 2*a*. Specifically, the third wheels 110*c* are arranged on inner side than the first and second wheels 110*a* and 110*b* so as not to interfere with the movement restriction parts 120.

In the embodiment, as illustrated in FIGS. 2 and 3, switching parts 130 are provided to switch between the state in which the movement of the control apparatus main body 2*a* is allowed and the state in which movement of the control apparatus main body 2*a* is restricted. Each of the switching parts 130 is arranged between the first wheel 110*a* and the third wheel 110*c*. Specifically, the switching parts 130 are provided at upper portions of the pair of leg portions 2*d*, respectively. When a doctor or the like steps on the switching part 130 downward with his/her foot, the movement restriction part 120 is moved in the direction perpendicular to the floor surface f. With this, the movement restriction part 120 can be switched between the state in which the movement restriction part 120 is in contact with the floor surface f (the movement restricted state) and the state in which the movement restriction part 120 is spaced away from the floor surface f (the movement allowed state).

In the embodiment, as illustrated in FIG. 1, provided between the pair of leg portions 2*d* is a foot unit 140 that includes: the operation pedals 22; and a foot unit base 141 to support the foot of a doctor who operates the operation pedals 22. Note that in FIGS. 2, 3, and 8, the foot unit 140 is omitted (not illustrated). The foot unit 140 has a substantially rectangular shape when viewed from below so as to fill the gap of the substantially U-shaped bottom surface 2*b* of the control apparatus main body 2*a*. The plurality of operation pedals 22 are arranged side by side on the far side of the foot unit base 141. The foot unit base 141 is provided with a notch 142 into which a leg of a chair (not illustrated) on which the doctor or the like sits can be inserted. The foot unit 140 is provided so as to be movable in the A1 and A2 directions with respect to the control apparatus main body 2*a* so that the position of the foot unit 140 can be adjusted with respect to the control apparatus main body 2*a* even when the movement of the control apparatus main body 2*a* is restricted by the movement restriction parts 120.

Figure 8:
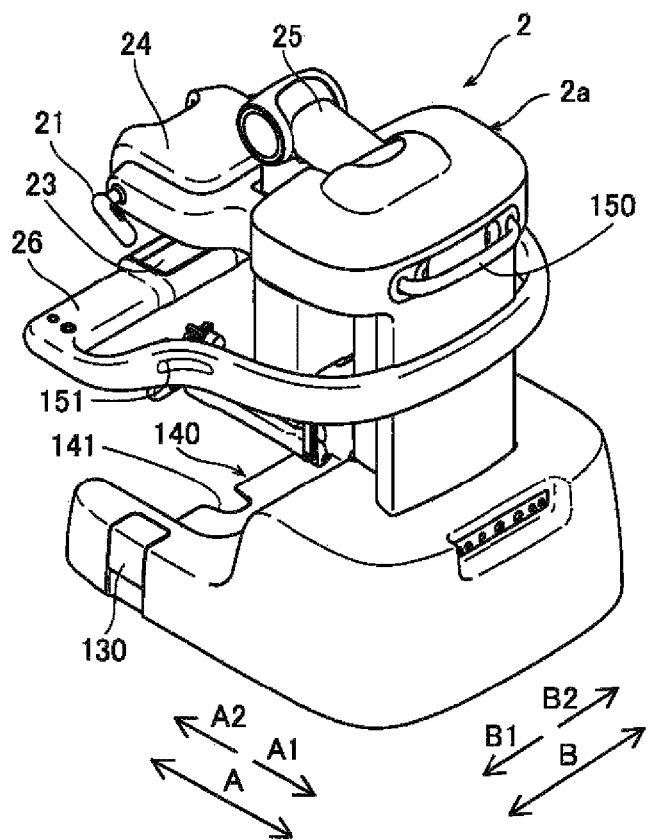
FIG. 8 is a diagram illustrating a perspective view of the remote control apparatus according to an embodiment as seen from the rear side.

In the embodiment, as illustrated in FIG. 8, the control apparatus main body 2*a* is provided with a grip portion 150 provided on a side (A1 side) of the control apparatus main body 2*a* opposite to a side of the control apparatus main body 2*a* operated by the doctor, the grip portion 150 being configured to be gripped to manually move the control apparatus main body 2*a*. The grip portion 150 has a substantially U-shape. The grip portion 150 is provided to extend along the B direction.

The support bar 26 is provided in a circumferential shape so as to surround the control apparatus main body 2*a*. Grip portions 151 are provided on the side surfaces of the support bar 26. The grip portion 151 has a hole shape. When the operator grips the grip portion 150 and moves the control apparatus main body 2*a*, the grip portion 151 may be supplementally used so that the operator can also grip the grip portion 151.

As illustrated in FIG. 1, the medical trolley 3 is provided with a control unit 31 that controls the operation of the medical manipulator 1 and a storage 32 that stores therein programs for controlling the operation of the medical manipulator 1. Based on the instruction inputted to the remote control apparatus 2, the control unit 31 of the medical trolley 3 controls the operation of the medical manipulator 1.

Further, the medical trolley 3 is provided with an input device 33. The input device 33 is configured to accept operations to move or change posture of a positioner 40, an arm base 50, and arms 60, mainly to prepare for surgery before the surgery.

As illustrated in FIG. 1, the medical manipulator 1 is placed in the surgery room. The medical manipulator 1 includes the medical trolley 3, the positioner 40, the arm base 50, and the arms 60. The arm base 50 is attached to a distal end of the positioner 40. The arm base 50 is a relatively long rod shape (elongate shape). Base portions (proximal end portions) of the arms 60 are attached to the arm base 50. Each of the arms 60 is configured such that the arm 60 is able to take a folded posture (storage posture). The arm base 50 and the arms 60 are used with being covered with a sterile drape (not illustrated).

The positioner 40 is configured as a 7-axis articulated robot. The positioner 40 is provided on the casing 34 of the medical trolley 3. The positioner 40 is configured to move the arm base 50. Specifically, the positioner 40 is configured to move the position of the arm base 50 three-dimensionally.

The positioner 40 includes a base portion 41 and link portions 42 connected to the base portion 41. The link portions 42 are connected to each other via joints 43.

To the distal end of each of the arms 60, the medical instrument 4 is attached. The medical instruments 4 include, for example, an instrument, an endoscope (not illustrated), and the like that are replaceable.

Figure 9:
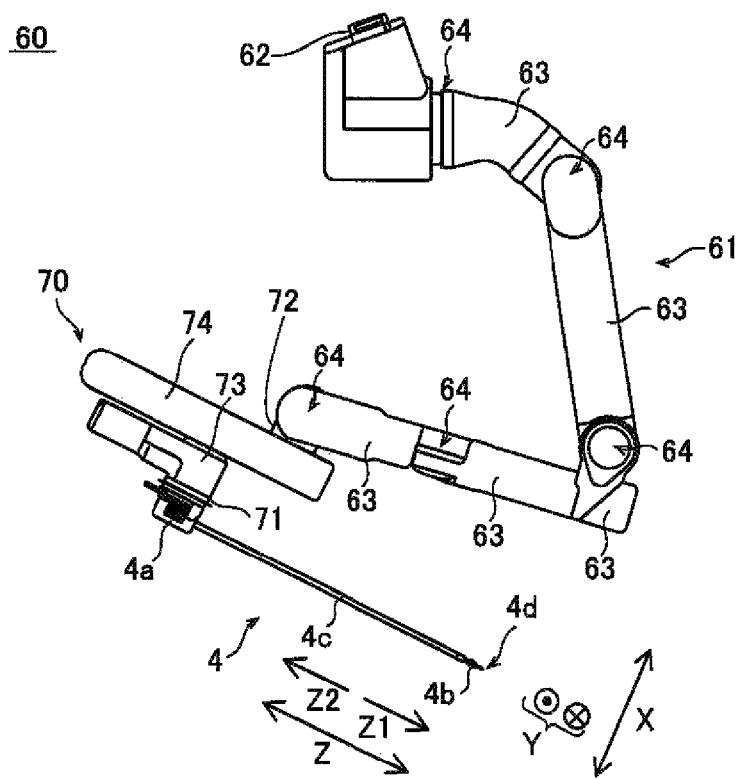
FIG. 9 is a diagram illustrating a view of a configuration of an arm of the medical manipulator according to an embodiment.

As illustrated in FIG. 9, the surgical instrument as the medical instrument 4 is provided with a driven unit 4a, which is driven by servo-motors provided in a holder 71 of the arm 60. To the distal end of the surgical instrument, an end effector 4b is provided. The end effector 4b, as a tool having one or more joints, includes, for example, a pair of forceps, a pair of scissors, a grasper, a needle holder, a micro dissector, a staple applier, a tacker, a suction and irrigation tool, a snare wire, a clip applier, and the like. The end effector 4b, as a tool having no joints, includes, for example, a cutting blade, an ablation probe, an irrigation device, a catheter, a suction orifice, and the like. The medical instrument 4 includes a shaft 4c that connects the driven unit 4a and the end effector 4b. The driven unit 4a, the shaft 4c, and the end effector 4b are arranged along the Z direction.

Next, the configuration of the arm 60 is described in detail.

As illustrated in FIG. 9, the arm 60 includes an arm section 61 (the base portion 62, the link portions 63, the joints 64) and a translation movement mechanism 70 provided at the distal end portion of the arm section 61. The arm 60 is configured such that the distal end portion thereof is three-dimensionally movable with respect to the proximal side (the arm base 50) of the arm 60. The plural arms 60 have the same configuration.

The translation movement mechanism 70 is provided on a side of the distal end of the arm section 61. The medical instrument 4 is attached to the translation movement mechanism 70. The translation movement mechanism 70 translationally moves the medical instrument 4 in an insertion direction of the medical instrument 4 into a patient P. The translation movement mechanism 70 is configured to translationally move the medical instrument 4 relative to the arm section 61. Specifically, the translation movement mechanism 70 is provided with the holder 71 configured to hold the medical instrument 4. The holder 71 accommodates therein the servo motors (not illustrated). The servo motors are configured to rotate rotors (rotation members) provided in the driven unit 4a of the medical instrument 4. The end effector 4b is operated by rotating the rotors (the rotation members) in the driven unit 4a.

The arm 60 is configured to be attachable to and detachable from the arm base 50.

The arm section 61 is configured as a 7-axis articulated robot arm. The arm section 61 includes the base portion 62 that connects the arm section 61 to the arm base 50 and the plural link portions 63 connected to the base portion 62. The plural link portions 63 are connected to each other via the joints 64.

The translation movement mechanism 70 is configured to translationally move the holder 71 along the Z direction so as to translationally move the medical instrument 4 attached to the holder 71 along the Z direction (the longitudinal direction of the shaft 4c). Specifically, the translation movement mechanism 70 includes a proximal side link unit 72 connected to the distal end of the arm section 61, a distal side link unit 73, and a connecting link unit 74 provided between the proximal side link unit 72 and the distal side link unit 73. The holder 71 is provided at the distal side link unit 73.

The connecting link unit 74 of the translation movement mechanism 70 functions as a double speed mechanism that moves the distal side link unit 73 relative to the proximal side link unit 72 along the Z direction. The translation movement mechanism 70 is configured to translationally move the medical instrument 4 attached to the holder 71 along the Z direction by moving the distal side link unit 73 relative to the proximal side link unit 72 along the Z direction. The distal end of the arm section 61 is configured such that the proximal side link unit 72 is connected thereto in such a manner that the proximal side link unit 72 is rotatable about a rotational axis extending in the Y direction orthogonal to the Z direction.

As illustrated in FIG. 1, the endoscope is attached to one of the plural arms 60 (for example, the arm 60b), and the medical instrument 4 other than the endoscope are attached to the other arms 60 (for example, the arms 60a, 60c, and 60d).

[Effects of Embodiment]

The following effects can be obtained in the embodiment.

In the embodiment, as described above, at the bottom surface 2b of the control apparatus main body 2a, the plurality of wheels 110 are provided which are configured to move the control apparatus main body 2a in the A direction parallel to the floor surface f on which the control apparatus main body 2a is placed and in the B direction parallel to the floor surface f and orthogonal to the A direction. With this, the control apparatus main body 2a can be moved in plural directions, that is, the A direction and the B direction orthogonal to each other along the floor surface f. Accordingly, the remote control apparatus 2 (the control apparatus main body 2a) can be easily located at a desired position in the operating room. As a result, it is possible to improve the convenience of moving the remote control apparatus 2.

Further, in the embodiment, as described above, the A direction is the direction in which the control apparatus main body 2a and the doctor who controls the control apparatus main body 2a are opposed to (face) each other. With this, since the control apparatus main body 2a can be moved in the direction in which the control apparatus main body 2a and the doctor face each other and in the left-right direction when viewed from the doctor, the control apparatus main body 2a can be easily aligned with the doctor.

Further, in the embodiment, as described above, as viewed from the bottom surface 2b of the control apparatus main body 2a, one or more of the plurality of wheels 110 is provided on the straight line L1 that is parallel to the B direction and passes through the gravity center G of the control apparatus main body 2a. With this, since at least one of the plurality of wheels 110 is arranged on the straight line L1 passing through the gravity center G, the control apparatus main body 2a can be supported by the plurality of wheels 110 in a well-balanced manner.

In the embodiment, as described above, further provided is the movement restriction parts 120 that are provided at the bottom surface 2b of the control apparatus main body 2a and are movable in the direction perpendicular to the floor surface f to switch between the state that allows the movement of the control apparatus main body 2a and the state that restricts the movement of the control apparatus main body 2a. The movement restriction parts 120 are provided on the straight line L1 that is parallel to the B direction and passes through the gravity center G of the control apparatus main body 2a when viewed from the bottom surface 2b of the control apparatus main body 2a. With this, the movement of the control apparatus main body 2a can be restricted by the movement restriction parts 120, so that the control apparatus main body 2a can be prevented from moving after the control apparatus main body 2a is positioned (during operation by the doctor, etc.). Also, since the movement restriction parts 120 are provided on the straight line L1 that is parallel to the B direction and passes through the gravity center G of the control apparatus main body 2a when viewed from the bottom surface 2b of the control apparatus main body 2a, the movement restriction parts 120 can support the control apparatus main body 2a and restrict the movement of the control apparatus main body 2a in a well-balanced manner.

Further, in the embodiment, as described above, each of the wheels 110 includes the wheel body 111 that rotates about the axis C1 thereof parallel to the B direction and the plurality of roller parts 112 that are arranged at the substantially equal angular intervals along the outer circumferential portion of the wheel body 111 and rotate about the axes C2 thereof parallel to the tangent line t1 of the circumferential locus t on which the wheel body 111 rotates. The wheels 110 are configured in such a manner that, when the control apparatus main body 2a is moved in the A direction, the wheel body 111 rotates about the axis C1 thereof parallel to the B direction and the plurality of roller parts 112 are revolved along with the rotation of the wheel body 111, whereas, when the control apparatus main body 2a is moved in the B direction, the wheel body 111 does not rotate and the plurality of roller parts 112 rotate about the axes C2 thereof parallel to the tangent line t1 of the circumferential locus t of the wheel body 111. With this, since the wheel 110 or the roller parts 112 rotates when the control apparatus main body 2a moves in either the A direction or the B direction, the control apparatus main body 2a can be easily moved in either the A direction or the B direction.

Further, in the embodiment, as described above, the plurality of roller parts 112 include the one-side roller parts 112a and the other-side roller parts 112b. The one-side roller parts 112a are arranged on one side in the B direction on the outer circumferential portion of the wheel body 111 and arranged at substantially equal angular intervals along the outer circumferential portion of the wheel body 111. The other-side roller parts 112b are arranged on the other side in the B direction on the outer circumferential portion of the wheel body 111 and arranged at substantially equal angular intervals along the outer circumferential portion of the wheel body 111 in such a manner that the other-side roller parts 112b are provided at angular positions different from the one-side roller parts 112a in the circumferential direction of the wheel body 111. With this, since the roller parts 112 are arranged in two rows with respect to the B direction, the load bearing capacity of the wheels 110 can be improved. Since the plurality of one-side roller parts 112a and the plurality of the other-side roller parts 112b are arranged at angle positions different from each other, any one of roller parts 112a and 112b among the one-side roller parts 112a and the other-side roller parts 112b can be in contact with the floor surface f when the wheel body 111 rotates. With this, rattling can be suppressed when the control apparatus main body 2a moves, and thus the control apparatus main body 2a can be smoothly moved in the B direction.

Further, in the embodiment, as described above, the bottom surface 2b of the control apparatus main body 2a is formed in the substantially U-shape including the body portion 2c and the pair of leg portions 2d extend from the body portion 2c along the floor surface f. The plurality of wheels 110 are provided on both the body portion 2c and the pair of leg portions 2d. With this, since the wheels 110 are provided on both the body portion 2c and the pair of leg portions 2d, the control apparatus main body 2a can be supported by the wheels 110 in a stable manner.

In the embodiment, further provided is the foot unit 140 that is provided between the pair of leg portions 2d and that includes the operation pedals 22 and the foot unit base 141 to support the foot of the doctor who operates the operation pedals 22. As a result, the medical manipulator 1 can be operated by using the operation pedals 22.

Further, in the embodiment, as described above, the plurality of wheels 110 include the pair of first wheels 110a respectively provided at the end portions of the pair of leg portions 2d, the pair of second wheels 110b respectively provided in the body portion 2c on the side opposite from the pair of leg portions 2d, and the pair of third wheels 110c respectively provided in the body portion 2c on the side closer to the pair of leg portions 2d. As a result, the control apparatus main body 2a can be supported in a more stable manner by the total of six wheels 110.

Further, in the embodiment, as described above, as viewed from the bottom surface 2b of the control apparatus main body 2a, the pair of third wheels 110c are provided on the straight line L1 that is parallel to the B direction and passes through the gravity center G of the control apparatus main body 2a. With this, since the pair of third wheels 110c are arranged on the straight line L1 passing through the gravity center G when viewed from the bottom surface 2b of the control apparatus main body 2a, the control apparatus main body 2a can be supported in a well-balanced manner with the pair of third wheels 110c.

Further, in the embodiment, as described above, further provided is the movement restriction parts 120 that are provided at the bottom surface 2b of the control apparatus main body 2a and are movable in the direction perpendicular to the floor surface f to switch between the state that allows the control apparatus main body 2a to move and the state that restricts the control apparatus main body 2a from moving. When viewed from the bottom surface 2b of the control apparatus main body 2a, the third wheels 110c are provided on inner side than the first wheels 110a and the second wheels 110b, and the movement restriction parts 120 are provided on outer sides than the third wheels 110c in the bottom surface 2b of the control apparatus main body 2a. With this, since the third wheels 110c are arranged inner (closer to the center than the end portion of the bottom surface 2b of the control apparatus main body 2a), the load of the control apparatus main body 2a can be easily supported with the third wheels 110c. Further, since the movement restriction parts 120 are arranged outer than the third wheels 110c that are arranged inner than the first and second wheels 110a and 110b, it is possible to prevent the movement restriction parts 120 from protruding outward from the side surfaces of the control apparatus main body 2a.

Further, in the embodiment, as described above, the switching parts 130 are further provided that are configured to switch between the state in which the movement restriction parts 120 allow the movement of the control apparatus main body 2a and the state in which the movement restriction parts 120 restrict the movement of the control apparatus main body 2a, and the switching parts 130 are arranged between the first wheels 110a and the third wheels 110c. With this, since the switching parts 130 are arranged between the first wheels 110a and the third wheels 110c, it is possible to prevent the switching parts 130 from protruding outward from the side surface of the control apparatus main body 2a.

Further, in the embodiment, as described above, the control apparatus main body 2a is further provided with the grip portion 150 provided on the side of the control apparatus main body 2a opposite to the side of the control apparatus main body 2a operated by the doctor, wherein the grip portion 150 is configured to be gripped to manually move the control apparatus main body 2a. As a result, an operator or the like who moves the control apparatus main body 2a can easily move the control apparatus main body 2a by gripping the grip portion 150 of the control apparatus main body 2a.

(Modifications)

Note that the embodiment disclosed herein should be interpreted as exemplary in every aspect and not limiting. The scope of the invention is indicated by claims, not by explanation of the embodiment described above, and includes equivalents to the claims and all alterations (modification) within the same.

For example, in the embodiment described above, the case has been described in which the remote control apparatus 2 is configured to be movable in the direction (A direction) in which the remote control apparatus 2 and the doctor operating the remote control apparatus 2 face each other. However, the disclosure is not limited thereto. In the disclosure, the remote control apparatus 2 may be configured to be movable in a first direction other than the direction in which the remote control apparatus 2 and the doctor operating the remote control apparatus 2 face each other, and in a second direction orthogonal to the first direction along the floor surface f.

Also, in the embodiment described above, the case has been described in which the pair of third wheels 110c are arranged on the straight line L1 passing through the gravity center G. However, the disclosure is not limited thereto. For example, a wheel(s) 110 other than the pair of third wheels 110c may be arranged on the straight line L1 passing through the gravity center G.

Also, in the embodiment described above, the case has been described in which the movement of the control apparatus main body 2a is restricted by the movement restriction parts 120 that are movable in the direction perpendicular to the floor surface f. However, the disclosure is not limited thereto. The movement of the control apparatus main body 2a may be restricted by a mechanism configured to lock the wheels 110 or the like.

Also, in the embodiment described above, the case has been described in which the wheels 110 are composed of Omni Wheel (registered trademark). However, the disclosure is not limited thereto. For example, the wheels 110 may be composed of casters or the like that can rotate 360 degrees.

Also, in the embodiment described above, the case has been described in which the bottom surface 2b of the control apparatus main body 2a has the substantially U-shape. However, the disclosure is not limited thereto. For example, the bottom surface 2b of the control apparatus main body 2a may have a quadrangular shape.

In the embodiment described above, the case has been described in which the number of the wheels 110 provided is six. However, the disclosure is not limited thereto. The number of the wheels 110 may be a number other than six (for example, four, eight, etc.).

In the embodiment described above, the case has been described in which the movement restriction parts 120 are provided on outer sides than the third wheels 110c in the bottom surface 2b of the control apparatus main body 2a. However, the disclosure is not limited thereto. The movement restriction parts 120 may be provided at positions (for example, a central part, etc.) other than the positions outer than the third wheels 110c in the bottom surface 2b of the control apparatus main body 2a In the embodiment described above, the switching part 130 is disposed between the first wheel 110a and the third wheel 110c. However, the disclosure is not limited thereto. The switching part 130 may be arranged at a position other than the position between the first wheel 110a and the third wheel 110c.

In the embodiment described above, the case has been described in which the number of the arms 60 provided is four. However, the disclosure is not limited thereto. The number of the arms 60 may be three or less.

In the embodiment described above, the case has been described in which each of the arm section 61 and the positioner 40 are configured as the 7-axis articulated robot. However, the disclosure is not limited thereto. For example, the arm 60 and the positioner 40 may be configured as articulated robots other than the 7-axis articulated robot (for example, a 6-axis articulated robot, an 8-axis articulated robot, or the like).

The invention claimed is:

1. A doctor-side control apparatus to be provided at a position away from a patient-side apparatus that includes a robotic arm to which a medical instrument is attached and to remotely control the patient-side apparatus, the doctor-side control apparatus comprising:
   a control apparatus main body; and a plurality of wheels provided at a bottom surface of the control apparatus main body, wherein
   each of the plurality of wheels is configured to move the control apparatus main body in a first direction parallel to a floor surface on which the control apparatus main body is placed and in a second direction parallel to the floor surface and orthogonal to the first direction,
   the plurality of wheels include a pair of first wheels, a pair of second wheels, and a pair of third wheels, wherein the pair of first wheels are respectively provided at end portions of a pair of leg portions, the pair of second wheels are respectively provided in a body portion on a side opposite from the pair of leg portions, and the pair of third wheels are respectively provided in the body portion at positions closer to the pair of leg portions than the pair of second wheels, and the pair of third wheels are arranged on a straight line that is parallel to the second direction and passes through the center of gravity of the control apparatus main body as seen from the bottom surface of the control apparatus main body.

2. The doctor-side control apparatus according to claim 1, wherein
the first direction is a direction in which the control apparatus main body and a doctor who controls the control apparatus main body face each other.

3. The doctor-side control apparatus according to claim 1, wherein
at least one of the plurality of wheels is provided on the straight line that is parallel to the second direction and passes through the center of gravity of the control apparatus main body as seen from the bottom surface of the control apparatus main body.

4. The doctor-side control apparatus according to claim 1, further comprising
a movement restriction part that is provided to the control apparatus main body and is movable in a direction perpendicular to the floor surface to switch between a state that allows movement of the control apparatus main body and a state that restricts the movement of the control apparatus main body, wherein
the movement restriction part is arranged on the straight line that is parallel to the second direction and passes through the center of gravity of the control apparatus main body as seen from the bottom surface of the control apparatus main body.

5. The doctor-side control apparatus according to claim 1, wherein
each of the wheels includes a wheel body that rotates about an axis thereof parallel to the second direction and a plurality of roller parts that are arranged at substantially equal angular intervals along an outer circumferential portion of the wheel body and rotate about axes thereof parallel to a tangent line of a circumferential locus on which the wheel body rotates,
when the control apparatus main body is moved in the first direction, the wheel body rotates about the axis thereof parallel to the second direction and the plurality of roller parts revolve along with the rotation of the wheel body, and
when the control apparatus main body is moved in the second direction, the wheel body does not rotate and the plurality of roller parts rotate about the axes thereof parallel to the tangent line of the circumferential locus on which the wheel body rotates.

6. The doctor-side control apparatus according to claim 5, wherein
the plurality of roller parts include one-side roller parts and the other-side roller parts, wherein the one-side roller parts are arranged on one side in the second direction at the outer circumferential portion of the wheel body and arranged at substantially equal angular intervals along the outer circumferential portion of the wheel body, and the other-side roller parts are arranged on the other side in the second direction at the outer circumferential portion of the wheel body and arranged at substantially equal angular intervals along the outer circumferential portion of the wheel body in such a manner that the other-side roller parts are provided at angular positions different from the one-side roller parts in a circumferential direction of the wheel body.

7. The doctor-side control apparatus according to claim 1, wherein
the bottom surface of the control apparatus main body is formed in a substantially U-shape including the body portion and the pair of leg portions extending from the body portion along the floor surface, and
the plurality of wheels are provided at the body portion and the pair of leg portions, respectively.

8. The doctor-side control apparatus according to claim 7, further comprising
a foot unit that is provided between the pair of leg portions and that includes operation pedals and a foot unit base to support a foot of a doctor who operates the operation pedals.

9. The doctor-side control apparatus according to claim 1, further comprising:
a grip portion provided on a side of the control apparatus main body opposite to a side of the control apparatus main body where a doctor operates, the grip portion being configured to be gripped to manually move the control apparatus main body.

10. The doctor-side control apparatus according to claim 1, wherein
the plurality of wheels are non-driving wheels, respectively.

11. A doctor-side control apparatus to be provided at a position away from a patient-side apparatus that includes a robotic arm to which a medical instrument is attached and to remotely control the patient-side apparatus, the doctor-side control apparatus comprising:
a control apparatus main body; and a plurality of wheels provided at a bottom surface of the control apparatus main body, wherein
each of the plurality of wheels is configured to move the control apparatus main body in a first direction parallel to a floor surface on which the control apparatus main body is placed and in a second direction parallel to the floor surface and orthogonal to the first direction,
the plurality of wheels include a pair of first wheels, a pair of second wheels, and a pair of third wheels, wherein the pair of first wheels are respectively provided at end portions of a pair of leg portions extending from a body portion along the floor surface, the pair of second wheels are respectively provided in the body portion on a side opposite from the pair of leg portions, and the pair of third wheels are respectively provided in the body portion at positions closer to the pair of leg portions than the pair of second wheels,
the doctor-side control apparatus further comprises movement restriction parts that are provided at the control apparatus main body and are movable in a direction perpendicular to the floor surface to switch between a state that allows movement of the control apparatus main body and a state that restricts the movement of the control apparatus main body, and
the third wheels are provided at positions inner than the first and second wheels in the bottom surface of the control apparatus main body, and the movement restriction parts are provided at positions outer than the third wheels in the bottom surface of the control apparatus main body.

12. The doctor-side control apparatus according to claim 11, further comprising
switching parts that are configured to switch between the state in which the movement restriction parts allow the movement of the control apparatus main body and the state in which the movement restriction parts restrict the movement of the control apparatus main body, wherein each of the switching parts is arranged between the corresponding first and third wheels.

13. A surgical system, comprising:
a patient-side apparatus that includes a robot arm to which a medical instrument is attached; and
a doctor-side control apparatus to be provided at a position away from the patient-side apparatus and to remotely control the patient-side apparatus, wherein
the doctor-side control apparatus comprising:
a control apparatus main body; and a plurality of wheels provided at a bottom surface of the control apparatus main body, wherein
each of the plurality of wheels is configured to move the control apparatus main body in a first direction parallel to a floor surface on which the control apparatus main body is placed and in a second direction parallel to the floor surface and orthogonal to the first direction,
the plurality of wheels include a pair of first wheels, a pair of second wheels, and a pair of third wheels, wherein the pair of first wheels are respectively provided at end portions of a pair of leg portions, the pair of second wheels are respectively provided in a body portion on a side opposite from the pair of leg portions, and the pair of third wheels are respectively provided in the body portion at positions closer to the pair of leg portions than the pair of second wheels, and
the pair of third wheels are arranged on a straight line that is parallel to the second direction and passes through the center of gravity of the control apparatus main body as seen from the bottom surface of the control apparatus main body.

14. The surgical system according to claim 13, wherein at least one of the plurality of wheels is provided on the straight line that is parallel to the second direction and passes through the center of gravity of the control apparatus main body as seen from the bottom surface of the control apparatus main body.

15. The surgical system according to claim 13, further comprising
a movement restriction part that is provided at the control apparatus main body and is movable in a direction perpendicular to the floor surface to switch between a state that allows the control apparatus main body to move and a state that restricts the control apparatus main body from moving, wherein
the movement restriction part is arranged on the straight line that is parallel to the second direction and passes through the center of gravity of the control apparatus main body as seen from the bottom surface of the control apparatus main body.

16. The surgical system according to claim 13, wherein
each of the wheels includes a wheel body that rotates about an axis thereof parallel to the second direction and a plurality of roller parts that are arranged at substantially equal angular intervals along an outer circumferential portion of the wheel body and rotate about axes thereof parallel to a tangent line of a circumferential locus on which the wheel body rotates, and
when the control apparatus main body is moved in the first direction, the wheel body rotates about the axis thereof parallel to the second direction and the plurality of roller parts revolve along with the rotation of the wheel body, and
when the control apparatus main body is moved in the second direction, the wheel body does not rotate and the plurality of roller parts rotate about the axes thereof parallel to the tangent line of the circumferential locus on which the wheel body rotates.

17. The surgical system according to claim 16, wherein the plurality of roller parts include one-side roller parts and the other-side roller parts, wherein the one-side roller parts are arranged on one side in the second direction at the outer circumferential portion of the wheel body and arranged at substantially equal angular intervals along the outer circumferential portion of the wheel body, and the other-side roller parts are arranged on the other side in the second direction at the outer circumferential portion of the wheel body and arranged at substantially equal angular intervals along the outer circumferential portion of the wheel body in such a manner that the other-side roller parts are provided at angular positions different from the one-side roller parts in a circumferential direction of the wheel body.

18. The surgical system according to claim 13, wherein the plurality of wheels are non-driving wheels, respectively.

* * * * *